United States Patent
Manzano-Rivera

(10) Patent No.: US 7,661,152 B2
(45) Date of Patent: Feb. 16, 2010

(54) GASTROSTOMY GARMENT

(76) Inventor: Raul Manzano-Rivera, Manati Chalets 116 Zeus St., Manati, PR (US) 00674

( * ) Notice: Subject to any disclaimer, the term of this patent is extended or adjusted under 35 U.S.C. 154(b) by 0 days.

(21) Appl. No.: 11/715,024

(22) Filed: Mar. 7, 2007

(65) Prior Publication Data

US 2008/0221525 A1    Sep. 11, 2008

(51) Int. Cl.
*A41F 9/00* (2006.01)
*A61F 5/44* (2006.01)

(52) U.S. Cl. .............................. 2/338; 2/114; 604/345

(58) Field of Classification Search ............... 604/174, 604/179, 345; 128/876; 2/338, 464, 114; 602/75

See application file for complete search history.

(56) References Cited

U.S. PATENT DOCUMENTS

| | | | | | |
|---|---|---|---|---|---|
| 2,476,513 | A | * | 7/1949 | Scott | 604/345 |
| 2,612,895 | A | * | 10/1952 | Magee | 604/327 |
| 2,788,785 | A | * | 4/1957 | Present | 604/345 |
| 2,793,368 | A | * | 5/1957 | Nouel | 450/119 |
| 3,160,158 | A | * | 12/1964 | Rayhart | 604/179 |
| 3,926,183 | A | * | 12/1975 | Spiro | 602/19 |
| 4,221,215 | A | * | 9/1980 | Mandelbaum | 604/327 |
| 4,470,410 | A | * | 9/1984 | Elliott | 128/877 |
| D277,986 | S | * | 3/1985 | Webb | D24/169 |
| 4,582,508 | A | * | 4/1986 | Pavelka | 604/179 |
| 4,596,560 | A | * | 6/1986 | Simpson | 604/174 |
| 4,666,432 | A | * | 5/1987 | McNeish et al. | 604/174 |
| 4,688,270 | A | | 8/1987 | Denicola et al. | |
| 4,698,848 | A | * | 10/1987 | Buckley | 2/114 |
| 4,738,661 | A | * | 4/1988 | Marut | 604/179 |
| 4,799,923 | A | * | 1/1989 | Campbell | 604/179 |
| 5,048,512 | A | * | 9/1991 | Turner et al. | 128/876 |
| 5,271,745 | A | * | 12/1993 | Fentress et al. | 604/179 |
| 5,304,145 | A | * | 4/1994 | Blair | 604/179 |
| 5,403,285 | A | * | 4/1995 | Roberts | 604/179 |
| 5,425,719 | A | * | 6/1995 | Lessing, Jr. | 604/179 |
| 5,468,229 | A | | 11/1995 | Chandler | |
| 5,496,282 | A | * | 3/1996 | Militzer et al. | 604/179 |
| 5,634,891 | A | * | 6/1997 | Beczak et al. | 602/19 |
| 5,669,884 | A | | 9/1997 | Bennes et al. | |
| 5,688,248 | A | * | 11/1997 | Lessing, Jr. | 604/179 |
| D393,310 | S | * | 4/1998 | Russo | D24/128 |
| 5,755,698 | A | * | 5/1998 | Kagan et al. | 604/179 |
| 5,853,396 | A | * | 12/1998 | Bennes et al. | 604/179 |
| 5,897,519 | A | * | 4/1999 | Shesol et al. | 602/79 |
| 6,032,289 | A | * | 3/2000 | Villapiano | 2/102 |
| D433,133 | S | * | 10/2000 | Dyer | D24/128 |

(Continued)

*Primary Examiner*—Alissa L Hoey
(74) *Attorney, Agent, or Firm*—Hector M. Reyes-Rivera

(57) ABSTRACT

A flexible belt-shape garment to be use around the torso of a person requiring a gastrostomy tube to be nourished is disclosed. The garment comprises a totally flexible main elongated body having an upper end, a lower end a first lateral side and a second lateral side, an outer surface and an inner surface intended to be in contact with the patient's body. It also comprises an aperture or opening in cooperative action with a flap cover that creates an internal pocket when close, wherein the gastrostomy tube is safely stored; a second mechanism for covering the internal pocket by overlapping the closed cover flap with of one of the lateral sides of the main body and optional ties or laces that are wrap around the installed belt and tie up for maximizing the protection of the gastrostomy tube and the stoma area.

18 Claims, 4 Drawing Sheets

U.S. PATENT DOCUMENTS

| | | | |
|---|---|---|---|
| 6,206,854 B1 * | 3/2001 | Weaver | 604/174 |
| 6,296,164 B1 * | 10/2001 | Russo | 224/602 |
| 6,460,187 B1 * | 10/2002 | Siegel | 2/114 |
| 6,477,710 B1 * | 11/2002 | Ojoyeyi | 2/69 |
| 6,579,268 B1 * | 6/2003 | Loining | 604/174 |
| D477,873 S * | 7/2003 | Borash et al. | D24/128 |
| 6,610,032 B1 * | 8/2003 | Prody | 604/179 |
| 6,681,404 B1 * | 1/2004 | Adlard et al. | 2/94 |
| 6,755,799 B2 * | 6/2004 | Toda | 602/19 |
| 7,418,741 B2 * | 9/2008 | Rogers | 2/114 |
| 2003/0065289 A1 * | 4/2003 | Clayton | 604/174 |
| 2003/0120216 A1 | 6/2003 | Bouphavichith et al. | |
| 2004/0163159 A1 * | 8/2004 | Edwards et al. | 2/338 |
| 2005/0059935 A1 * | 3/2005 | Yamazaki et al. | 604/179 |
| 2005/0107745 A1 | 5/2005 | Enroth | |
| 2006/0084923 A1 * | 4/2006 | Lotartaro | 604/179 |
| 2006/0218690 A1 * | 10/2006 | James | 2/69 |
| 2006/0224131 A1 | 10/2006 | Calvert | |

\* cited by examiner

GASTROSTOMY GARMENT

BACKGROUND OF THE INVENTION

The present invention relates to medical dressings or medical garments for use on patients who have had gastrostomy procedure. More particularly, the invention is directed to a flexible belt-shape garment for use around the torso of a person requiring feeding means such as a gastrostomy tube or G-tube, in order to provide storing, protection and safety to the said feeding means and the area surrounding the same.

Gastrostomy is a well know surgical procedure performed on patients that temporarily or permanently require to be fed directly through a tube connected to the stomach. Among the reasons requiring a patient to be subjected to a gastrostomy procedure are conditions such as birth defects of the mouth, esophagus or stomach. Similarly, other patients requiring the said procedure are those suffering from conditions such as neuromuscular conditions that cause people to eat very slowly due to the shape of their mouth or a weakness affecting their chewing and swallowing muscles as well as obstructions of the stomach outlet into the small intestine caused by different reasons such as peptic ulcers or tumor.

The main objective of the gastrostomy process is the insertion of the feeding means through the abdomen wall and into the stomach via an external opening called stoma. Generally speaking, the feeding means comprises a feeding tube, known as G-tube, through which food or nutrients are introduced to the patient's stomach and through which fluids may also be vented from the patient's stomach.

Among the risks of the procedure are the infections, bleeding and accidental dislodgment of the tube. Thus, there is a need to maintain the G-tube and the stoma area clean, protected and manageable. It would be helpful and advantageous to provide a cover belt-shape and flexible garment having three security measures to store, hide and protect the G-tube and stoma area of the patient once it is wrapped around the patient's torso. It would be further advantageous to provide a belt like garment that is made of soft, flexible materials, easy to wear, inexpensive, washable and reusable.

SUMMARY OF THE INVENTION

It is an object of the present invention to protect the feeding means such as G-tube and stoma area located on the torso of a gastrostomy's patient from damage, contamination and accidental extraction by providing a flexible, reusable, comfortable belt-shape garment to be used around the torso of the wearer.

Another object of the invention is to provide an inexpensive, reusable, washable, comfortable belt that comprises means to safely store and hide the G-tube, in such a way that it cannot be visibly detected when worn conventional garments.

Still another object of the invention is to provide a belt, which has at least three different security closing elements to protect the G-tube and stoma of a patient, said elements comprising an easy to open and close flap cover located over an aperture on the said belt, a closing means or fastening means at the extremes or distal edges of the belt and at least two ties, strings or laces that may be wrap around the torso and tied up over the belt.

A further object of this invention to provide a flexible belt having a flexible and easy manageable storing area for the g-tube, wherein it may be stored whenever it is not in use and wherein it is totally accessible, in such a way that the said G-tube may be easily retrieved for its intended use and conveniently returned and safely store again when the said tube is not in use without the need of removing the said belt.

Another object of the invention is to provide a belt that is easily changeable or removable and conveniently adjustable to the user's torso, accommodating its shape to the user's contour.

Yet another object of the invention is to provide a belt that is friendly usable, washable, durable and easy to clean in order to maintain cleanliness and proper sanitary conditions around the G-tube and stoma region of gastrostomy patients in order to protect the said G-tube and stoma region from external germs and bacteria, and to promote and enhance the user's health, self esteem and personal confidence.

Even another object of the invention is to provide a belt that smoothly fits or adjusts itself to the contour of the patient's body, without forming a noticeable bulkiness and allows maximum freedom of bodily movements of the patient/wearer in such a way that it may be worn with conventional garments without being noticeable while simultaneously maintaining the stoma region underneath it.

These and other objects of the instant invention are accomplished by providing a totally flexible belt-shape garment to be used around the torso of a person that had been subjected to a gastrostomy procedure and requires a G-tube or similar feeding means in order to provide protection, storing and safety to the G-tube of the wearer even from the very beginning of the post operative period or after the stoma wound has healed. The said garment comprises a totally flexible main elongated body having an upper end, a lower end a first lateral side and a second lateral side, an outer surface and an inner surface intended to be in contact with the patient's body. The said elongated body comprises an elastic band integrated and preferably located substantially at the center of the said upper end; an aperture or opening located on the said main body, wherein the said aperture or opening is intended to be positioned over the patient's stoma. It also comprises a flap cover made of the same or similar flexible material as the said belt main body; which is located at the said outer surface of the said main body and on top of the said aperture or opening so that the said cover flap may safely close or open the said opening or aperture giving immediately access to the stoma and wherein once the said flap cover is in a closed position, a flexible internal pocket is formed between the flap cover and the surface of the said outer surface that is covered by the said flap cover, wherein the G-tube may be safety stored in the said pocket.

The belt-shape garment also comprises means for safely closing the flap cover in cooperation with fastening means on the said outer surface of the belt, thus securing the g-tube when it is not in use and means for adjusting and closing the said belt around the torso of a person. Optionally, the belt also comprises at least two elongated ties, strings or laces located on the said outer surface that are crossed over or wrapped around the said main body of the garment and which extremes or ends are tied up in order to secure the belt to the patient's torso.

BRIEF DESCRIPTION OF THE DRAWINGS

The invention will be described in further detail herein after with reference to the illustrative preferred embodiments shown in the accompanying following drawings, which are included for illustrative purposes without limiting the invention in any manner.

DETAILED DESCRIPTION OF THE PREFERRED EMBODIMENTS

Detailed embodiments of the instant invention are disclosed herein, however it is to be understood that the disclosed embodiments are only examples and that the disclosed invention may be embodied in alternative forms and/or in other possible variations. The particular structural and/or functional details disclosed herein should not be interpreted as limiting, since they are presented as a basis for the claims and with the main objective of teaching those skilled in the art to make and use the instant invention. Particularly, shapes, length and width of the invention may be variable without departing from the spirit of the invention and such modifications are indeed embraced in the scope of the instant invention.

Figure 1:
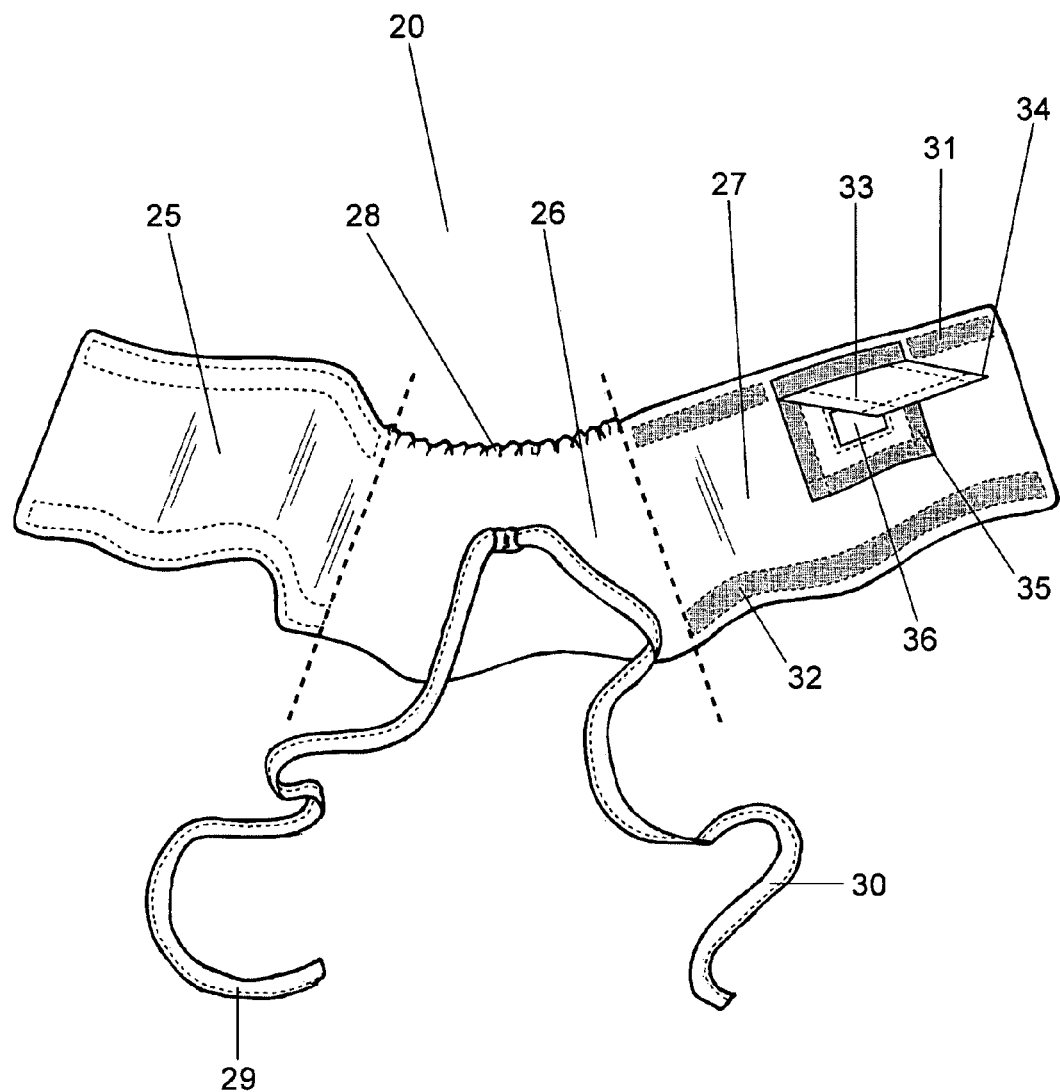
FIG. 1 shows a graphical representation of top view of a stereotype of the belt-shape garment of the instant invention, illustrating the outer surface of the garment according to the instant invention.
Figure 2:
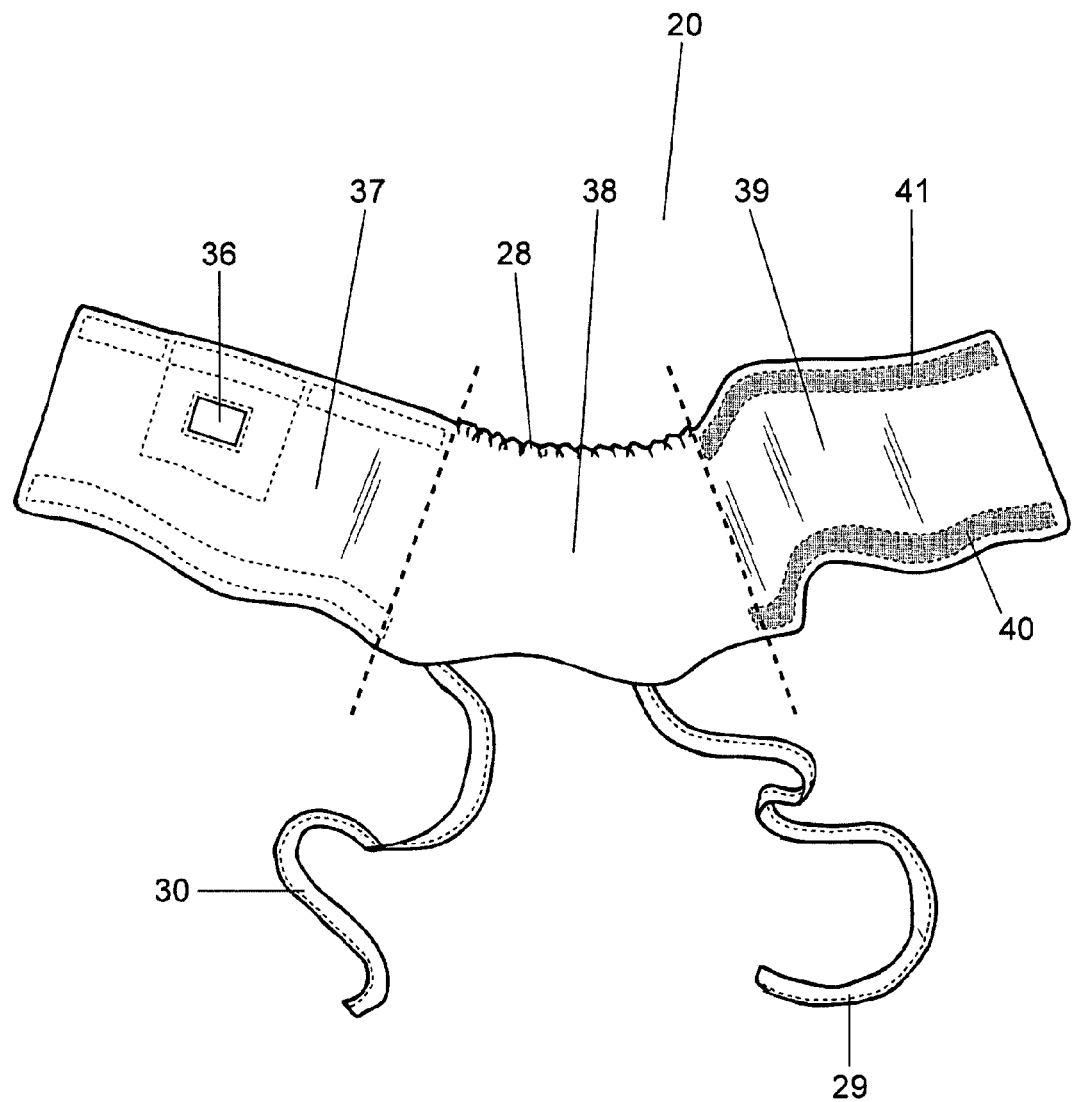
FIG. 2 shows a graphical representation of top view of a stereotype of the belt-shape garment of the instant invention, illustrating the inner surface of the garment according to the instant invention.

Referring now to the accompanying figures, and in particular to FIGS. 1 and 2, wherein the belt-shape garment 20, from now on referred also as the belt 20, is shown according to the principles of the present invention. On FIG. 1, the outer surface of elongated body of the belt 20 is shown and it has been divided in section 25, section 26 and section 27 for illustrative purposes only. Similarly, the reverse or inner surface of belt 20 is shown in FIG. 2, and the said surface has been imaginarily divided as section 37, section 38 and section 39 in order to properly identified particular sections of belt 20 for illustrative purposes only.

The said main body of belt 20 is made of multiple layers of flexible fabrics sewn together, one on top of the other. The said fabric layers are preferably sewn following the margins or edges of the said elongated body. Fabrics that are breathable, non allergic, adsorbent, flexible yet strong and firm are highly preferred. Even more preferred is the use of cotton fabric or cotton containing fabrics having a stronger but still flexible texture. In the even more preferred embodiment, an interfacing fabric which is firm, yet flexible is placed in the middle of less sturdy and more flexible fabric layers before sewing them to produce the said main body. The use of interfacing, term well known in the art of fabrics, adds firmness, strength and shape to the main body while maintaining its flexibility. As well known in the art of fabrics and clothes, interfacing is a common term for a variety of fabrics used on the unseen or "wrong" side of fabrics in sewing. Interfacings can be used to stiffen or add body to fabric, such as the interfacing used in shirt collars; to strengthen a certain area of the fabric, for instance where buttonholes will be sewn; or to keep fabrics from stretching out of shape. Interfacings come in a variety of weights and stiffnesses to suit different purposes.

Fastening means 31 and 32, located on upper and lower section of section 27 in cooperation with fastening means 41 and 40 placed on section 39 are shown in FIGS. 1 and 2. The said fastening means are illustrated as sewn strips of Velcro®, nonetheless any other suitable fastening means may be used in order to allow the wearer of the belt to adjust and secure belt 20 around his or her torso. For instance, fastening means such as hook and loops, button, button and holes, zippers, garments snaps, and similar others may be used alone or in combination. Similarly, the location of the said fastening means over the main body of belt 20 may be different to the one illustrated in FIGS. 1 and 2, without departing from the spirit of the present invention.

Additionally, belt 20 comprises at least two strings, ties or laces 29 and 30. The terms strings, ties and laces are used as equivalents terms to describe fastening means represented in numerals 29 and 30, which may be optional in functional terms. The said strings, ties or laces may be made from cotton fabrics, cotton containing fabrics or any other suitable material; but more preferably from cotton fabrics or cotton containing fabrics. They are connected to belt 20 by sewing one of their edges or extremes to the outer surface of belt 20 while leaving the other extreme or edge free as illustrated in FIG. 1. More preferably, they are connected to belt 20 by sewing one of their extremes or edges on substantially the middle of central section 26, as illustrated in FIG. 1. As illustrated in FIGS. 4C and 4D, once the belt is wear around the torso of the user, the said strings, laces or ties are wrapped around the wearer's torso but over the body of the belt 20 and their free edges or extremes are tied up to further secure the said belt.

As illustrated on FIG. 1, section 26 and on FIG. 2, section 38, on the center section of the main body, an elastic band 28 is sewn on the upper end of belt 20. The said elastic band 28 allows more flexibility to the main body of belt 20, and further allowing that the belt 20 fits to the contour of the user's body, facilitating the wearer's body to move freely.

Figure 3:
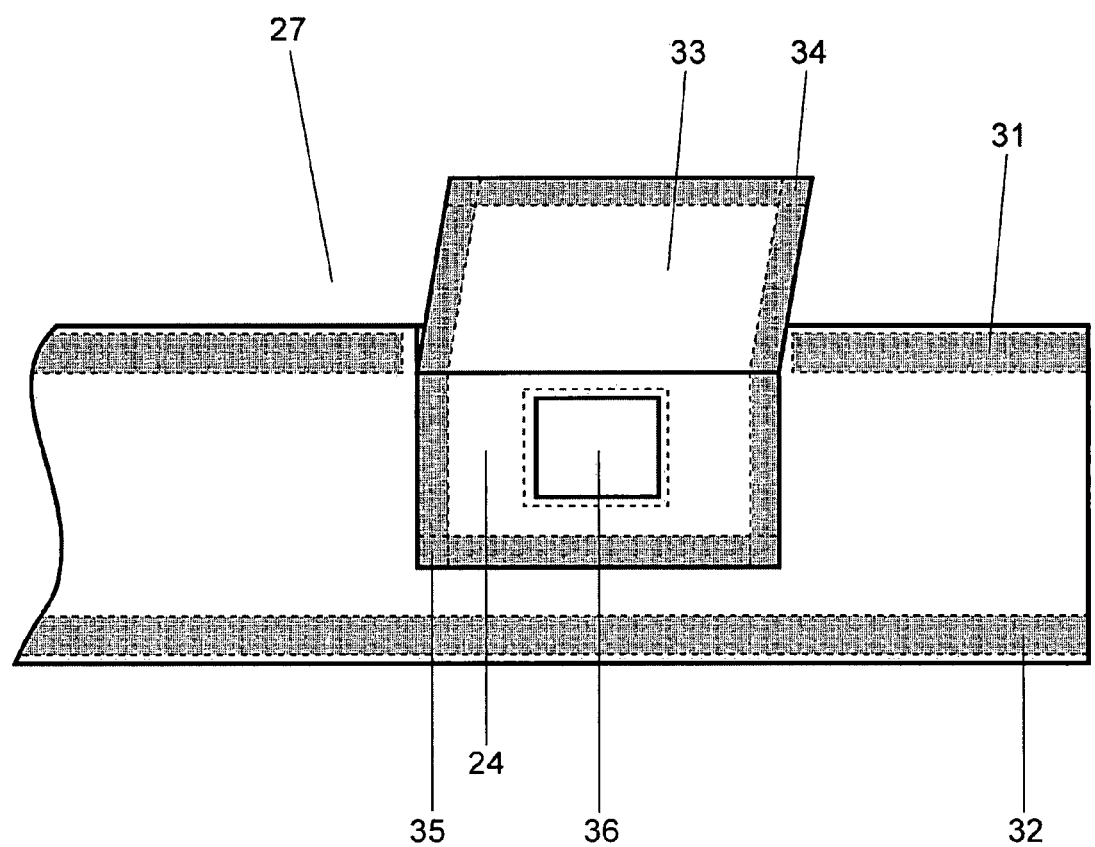
FIG. 3 shows a graphical representation of top view of a stereotype of the belt-shape garment of the instant invention, illustrating in detail the section of the belt-like garment to be positioned directly over stoma.

Section 27 of belt 20 shown in FIG. 1, is further illustrate in more detail on FIG. 3, wherein it is shown that belt 20 also comprises an aperture or opening 36 through its surface. The edges around the aperture or opening 36 are sewn to close the interior of the fabric layers forming the main body of the belt 20, as shown by the lines around the edges of said opening 36 on FIG. 3. The said aperture or opening 36 is intended to allow convenient access to the region of the wearer's stoma. On top of the aperture or opening 36, there is a flap cover 33, made of the same or similar flexible fabrics used in the preparation of main body of the belt 20. More particularly, the said flexible flap cover is made of multiple flexible fabrics layers sewn around the edges, as illustrated on FIG. 3. The said flap cover 33 is sewn on the upper part of section 27. Around the edges of the said cover flap 33, there are fastening means 34 in cooperation with fastening means 35, located over outer surface of section 27, in such a way that once the flap cover 33 is lowered toward the opening 36 in order to securely close the said opening 36, the said fastening means 34 and 35 cooperatively maintain the flap cover 33 on the surface of 27, covering opening 36 completely and firmly.

Once the flap cover 33 is in the closing position, the area of the outer surface of section 27 which is between the aperture or opening 36 and the fastening means 35, illustrated with numeral 24 and the flap cover 33 creates or forms an internal pocket, wherein the wearer of the belt 20 may safely store the g-tube in different manners, for instance it may be curled the said g-tube in the said pocket. Thus, if the G-tube is not in use, it may remain safely stored in the said pocket. Furthermore, it may be conveniently retrieved for its intended use by opening the said flap cover 33 without the need to remove the belt 20 from the user's torso or waist. Size and shape of the opening or aperture 36 as well as the flap cover 33 may be variable as long as the intended purpose of providing easy access to the stoma area and creating a storing G-tube storing internal pocket are accomplished.

Regarding cooperative fastening means 34 and 35 on outer surface and on flap cover 33 respectively, they are illustrated as strips of Velcro® sewn to the corresponding area. However, strips of any other fastening material, as well as any other suitable fastening means such as buttons, buttons and holes, hooks and loops, garments snaps, zippers and others may be used.

Length and width of belt 20 may be manufactured in different sizes so that it may fit to any prospective user. Belt 20 widths may be proportional to the length in the approximate ratio as shown in the drawings or it may be larger. Optionally, conventional pockets may be added to the main body of belt 20, providing place to safe gauzes, medicaments or the like.

Figure 4:
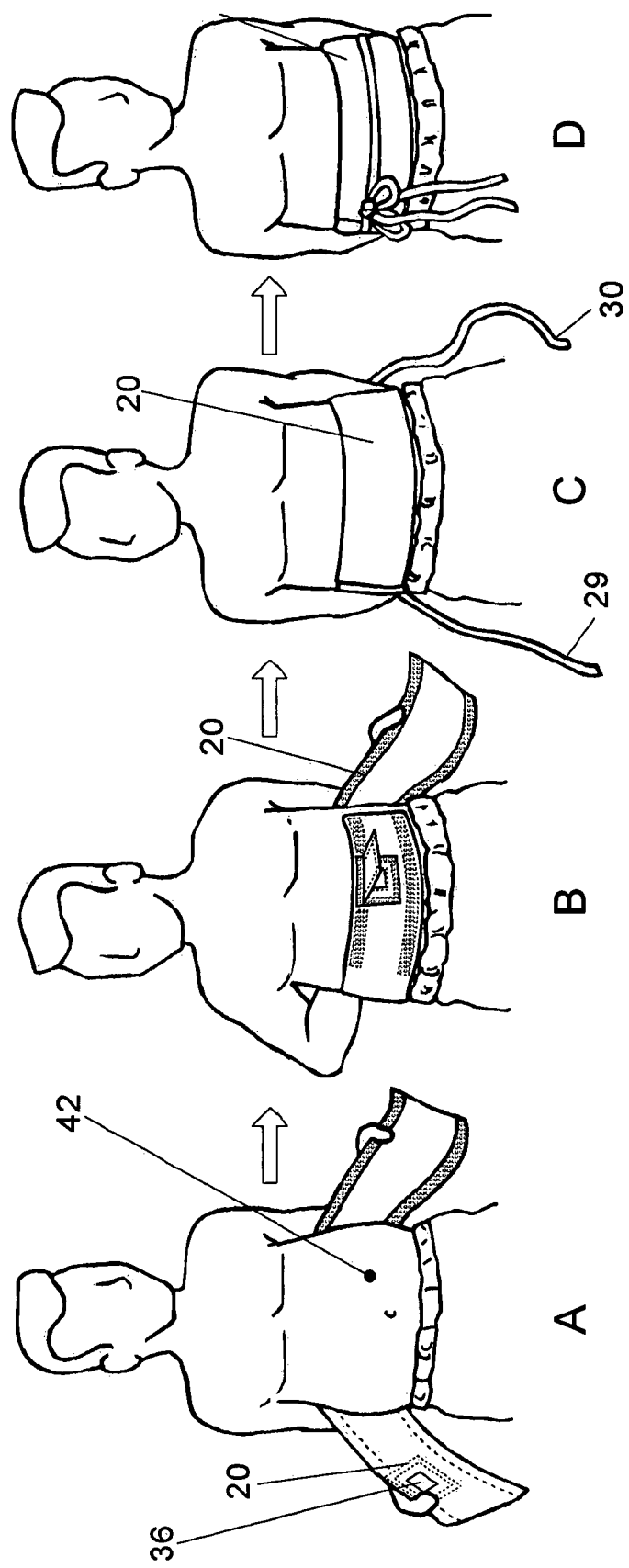
FIG. 4A-4D shows a graphical representation illustrating the installation of the belt shape garment according to the invention by a person having a g-tube.

FIG. 4 illustrates the use of the belt 20 according to the invention. FIG. 4 shows the installation of belt 20 on a wearer's torso following steps 4A through 4D. Initially, the belt 20 is openly extended over the wearer's back, and opening 36 is positioned over the wearer's stoma, identified as numeral 42, wherein the G-tube (not illustrated) is located. Once the G-tube is secured on the pocket formed by closing the flap cover 33, the belt 20 is adjusted and secured to the wearer's torso by fastening the fastening means 31, 32 40 and 41 as illustrated in FIGS. 4B and 4C. Thus, the internal pocket formed by the closed flap cover 33 creates the first mechanism of protecting and storing the g-tube and the stoma area while overlapping section 27 with section 39 results a second covering of the stoma region as illustrated in FIGS. 4B and 4C. Once fastened, the strings, ties or laces 29 and 30 are tied up around the torso or waist of the wearer, which is a third protecting means of the g-tube and stoma area, as illustrated on FIG. 4D.

While the invention has been described with reference to preferred embodiments, it will be understood by those skilled in the art that various changes may be made and equivalents may be substituted for elements thereof without departing from the scope of the invention. In addition, many modifications, particularly in shape or size may be made to adapt a particular situation or material to the teachings of the invention without departing from the essential scope thereof. Therefore, it is intended that the invention not be limited to the particular embodiment disclosed as the best modes contemplated for carrying out the invention, but that the invention will include all embodiments falling within the scope of the appended claims.

What is claimed is:

1. A flexible belt-shaped garment for use on patients requiring feeding means protruding form said patient's torso; such as a gastrostomy tube, wherein said garment comprises:
   a) a flexible elongated body comprising an upper end, a lower end, a first lateral side and a second lateral side, an outer surface and an inner surface;
   b) an elastic band integrated on said upper end;
   c) an aperture or opening located on said elongated body;
   d) a flexible flap cover, located at said outer surface and on top of said aperture or opening;
   e) a first fastening means system for fastening said flap cover to the outer surface of said flexible elongated body, so that once said flap cover is in the closed position, the opening or aperture is safely and firmly closed and wherein said flap cover and a section of the outer surface covered by said flap cover in the closed position creates a flexible pocket for safely storing the gastrostomy tube;
   f) a second fastening means for fastening and securing said elongated body around the torso of a patient, wherein said second fastening means are located in a cooperative way at the first lateral side and the second lateral side of said flexible elongated body and;
   g) a third fastening means comprising at least two elongated flexible ties, strings or laces; wherein one of the edges or extremes of said ties, strings or laces are located at the center on said outer surface of said flexible elongated body and wherein the free section of said ties, strings or laces may be wrapped around the torso of the wearer and over said belt and the free edges or extremes of said ties, strings or laces are tied up to further secure the belt.

2. The flexible belt shaped garment as recited in claim 1, wherein said elastic band is integrated substantially at the center of the upper end.

3. The flexible belt-shaped garment as recited in claim 1, wherein said elongated flexible ties, strings or laces are made of cotton fabric or cotton containing fabrics.

4. The flexible belt-shaped garment as recited in claim 1 wherein said elongated body is made of multiple flexible fabric layers, sewn and containing a fabric interfacing layer in the middle of said flexible fabric layers.

5. The flexible belt-shaped garment as recited in claim 4, wherein the flexible fabric layers sewn are made of cotton or cotton containing fabrics.

6. The flexible belt-shaped garment as recited in claim 4, wherein said flexible flap cover is made of multiple flexible fabric layers sewn.

7. The flexible belt-shaped garment as recited in claim 1, wherein said first fastening means are selected from hook and loop fasteners, garments snaps, buttons or buttons and holes.

8. The flexible belt-shaped garment as recited in claim 7, wherein said first fastening means are hook and loop fasteners.

9. The flexible belt-shaped garment as recited in claim 1, wherein said second fastening means are selected from hook and loop fasteners, garments snaps, buttons or buttons and holes.

10. The flexible belt-shaped garment as recited in claim 9, wherein the second fastening means are hook and loop fasteners.

11. A belt-shaped garment to be used around the torso of a person requiring a gastrostomy tube in order to provide protection, storing and safety to said gastrostomy tube and stoma area of the wearer; wherein said belt-shaped garment comprises a flexible elongated body made of flexible layers of fabric sewn one on top of each other and having a fabric interface layer in the middle of the flexible layers of fabric; said elongated body comprising an upper end, a lower end, a first lateral side and a second lateral side, an inner surface and an outer surface; wherein said flexible elongated body further comprising:
   a) an elastic band integrated substantially at the center of said upper end;
   b) at least two elongated ties or laces located on said outer surface;
   c) an aperture or opening located on the elongated body;
   d) a flap cover made of the same flexible material as that of the elongated body, located at the outer surface and on top of said aperture or opening so that said cover flap may safely close or open the opening or aperture and wherein once said flap cover is in a closed position, a flexible internal pocket is formed between the flap cover and a surface of the outer surface covered by said flap cover wherein the gastrostomy tube may be safely stored;

e) a first fastening means for safely closing the flap cover to said outer surface;

f) a second fastening means for securing the first lateral side and the second lateral side of said elongated body around the torso of a person;

wherein said flap cover, said means for securing the elongated body and said ties, or laces are altogether three different mechanisms to safely protect the person's gastrostomy tube and stoma area.

12. A belt-shaped garment to be used around the torso of a person requiring a gastrostomy tube in order to provide protection, storing and safety to said gastrostomy tube and stoma area of the wearer; wherein said belt-shaped garment comprises:

a) a non-bulky, flexible main unit, totally made of fabric, said main unit comprising an elongated body and a non-bulky, flexible interface layer;

wherein said elongated body is made out of flexible layers of fabric sewn one on top of each other and comprises an upper end, a lower end, a first lateral side, a second lateral side, an inner surface and an outer surface and wherein said fabric interface layer is located entirely at the inner surface of said elongated body;

b) an elastic band, integrated substantially at the center of said upper end;

c) an aperture or opening located on the elongated body;

d) a non-bulky, fabric flap cover made out of flexible layers of fabric sewn one on top of each other; said fabric flap comprising a fabric interface in the entire internal area of the flexible layers of fabric that make up said fabric flap cover, wherein said non-bulky, fabric flap cover is located at said outer surface of said elongated body and on top of the aperture or opening so that said flap cover may safely close or open said opening or aperture and wherein once said flap cover is in a closed position, a flexible internal pocket is formed between that flap cover and a surface of said outer surface covered by the flap cover wherein the gastrostomy tube may be safely stored;

e) a first fastening means for safely closing the flap cover to said outer surface;

f) a second fastening means for securing said first lateral side and said second lateral side of the elongated body around the torso of a person;

wherein said fabric flap cover and said means for securing the elongated body are two different mechanisms to safely protect the person's gastrostomy tube and stoma area.

13. The flexible belt-shaped garment as recited in claim 12, wherein said first fastening means are selected from hook and loop fasteners, garments snaps, buttons or buttons and holes.

14. The flexible belt-shaped garment as recited in claim 13, wherein said first fastening means are hook and loop fasteners.

15. The flexible belt-shaped garment as recited in claim 12, wherein said second fastening means are selected from hook and loop fasteners, garments snaps, buttons or buttons and holes.

16. The flexible belt-shaped garment as recited in claim 15, wherein the second fastening means are hook and loop fasteners.

17. A non-bulky belt-shaped garment to be used around the torso of a person requiring a gastrostomy tube in order to provide protection, storing and safety to said gastrostomy tube and stoma area of the wearer; wherein said belt-shaped garment comprises:

a) a main unit, made totally of fabric, said main unit comprising an elongated body made out of layers of fabric sewn one on top of each other, an upper end, a lower end, a first lateral side, a second lateral side, an inner surface and an outer surface;

b) a fabric interface layer located entirely at the inner surface of said elongated body;

c) an elastic band, integrated substantially at the center of said upper end;

d) an aperture or opening located on the elongated body;

e) a flap cover made out of layers of fabric sewn one on top of the other and having a fabric interface in the entire internal area of the layers of fabric that make up said fabric flap cover and wherein said flap cover is located at said outer surface and on top of said aperture or opening so that said flap cover may safely close or open said opening or aperture and wherein once said flap cover is in a closed position, an internal pocket is formed between the flap cover and a surface of said outer surface covered by the flap cover wherein the gastrostomy tube may be safely stored;

f) a first fastening means for safely closing the flap cover to said outer surface;

g) a second fastening means for securing said first lateral side and said second lateral side of the elongated body around the torso of a person.

18. A non-bulky belt-shaped garment to be used around the torso of a person requiring a gastrostomy tube in order to provide protection, storing and safety to said gastrostomy tube and stoma area of the wearer; the said belt-shaped garment consisting essentially of:

a) a main unit, made totally of fabric, said main unit comprising an elongated body made out of layers of fabric sewn one on top of each other, an upper end, a lower end, a first lateral side, a second lateral side, an inner surface and an outer surface;

b) a fabric interface layer located entirely at the inner surface of said elongated body;

c) an elastic band, integrated substantially at the center of said upper end;

d) an aperture or opening located on the elongated body;

e) a flap cover made out of layers of fabric sewn one on top of the other and having a fabric interface in the entire internal area of the layers of fabric that make up said fabric flap cover and wherein said flap cover is located at said outer surface and on top of said aperture or opening so that said flap cover may safely close or open said opening or aperture and wherein once said flap cover is in a closed position, an internal pocket is formed between the flap cover and a surface of said outer surface covered by the flap cover wherein the gastrostomy tube may be safely stored;

f) a first fastening means for safely closing the flap cover to said outer surface;

g) a second fastening means for securing said first lateral side and said second lateral side of the elongated body around the torso of a person.

* * * * *

UNITED STATES PATENT AND TRADEMARK OFFICE
CERTIFICATE OF CORRECTION

PATENT NO. : 7,661,152 B2
APPLICATION NO. : 11/715024
DATED : February 16, 2010
INVENTOR(S) : Raul Manzano-Rivera It is certified that error appears in the above-identified patent and that said Letters Patent is hereby corrected as shown below:

Title Page, Item (57) abstract, please replace the phrase "belt-shape" with the phrase "belt-shaped".

Title Page, Item (57) abstract, please replace the phrase "use around" with the phrase "used around".

Title Page, Item (57) abstract line 6, please replace the phrase "when close" with the phrase "when closed".

Title Page, Item (57) abstract line 12 , please replace the phrase "wrap around" with the phrase "wrapped around".

Title Page, Item (57) abstract line 13, please replace the phrase "tie up for" with the phrase "tied up for".

Column 1, line 6 of the specification, please replace the phrase "had gastrostomy" with the phrase "had a gastrostomy".

Column 1, line 8 of the specification, please replace the phrase "belt-shape" with the phrase "belt-shaped".

Column 1, line 12 of the specification, please replace the phrase "well know" with the phrase "well known".

Column 1, line 28 of the specification, please replace the phrase "as G-tube" with the phrase "as a G-tube".

Column 1, line 45 of the specification, please replace the phrase "as G-tube" with the phrase "as a G-tube".

Column 1, line 48 of the specification, please replace the phrase "belt-shape" with the phrase "belt-shaped".

Signed and Sealed this

Twenty-second Day of June, 2010

David J. Kappos
*Director of the United States Patent and Trademark Office*

CERTIFICATE OF CORRECTION (continued)
U.S. Pat. No. 7,661,152 B2

Column 1, line 53 of the specification, please replace the phrase "worn conventional" with the phrase "worn under conventional".

Column 1, line 61 of the specification, please replace the phrase "wrap around" with the phrase "wrapped around".

Column 1, line 65 of the specification, please replace the phrase "g-tube" with the phrase "G-tube".

Column 2, line 9 of the specification, please replace the phrase "friendly usable" with the phrase "user friendly".

Column 2, line 24 of the specification, please replace the phrase "belt-shape" with the phrase "belt-shaped".

Column 2, line 50 of the specification, please replace the phrase "belt-shape" with the phrase "belt-shaped".

Column 2, line 52 of the specification, please replace the phrase "g-tube" with the phrase "G-tube".

Column 3, line 2 of the specification, please replace the phrase "belt-shape" with the phrase "belt-shaped".

Column 3, line 6 of the specification, please replace the phrase "belt-shape" with the phrase "belt-shaped".

Column 3, line 10 of the specification, please replace the phrase "belt-shape" with the phrase "belt-shaped".

Column 3, line 14 of the specification, please replace the phrase "belt-shape" with the phrase "belt-shaped".

Column 3, line 34 of the specification, please replace the phrase "belt-shape" with the phrase "belt-shaped".

Column 4, line 25 of the specification, please replace the phrase "wear around" with the phrase "worn around".

Column 4, line 61 of the specification, please replace the phrase "g-tube" with the phrase "G-tube".

Column 4, line 62 of the specification, please replace the phrase "g-tube" with the phrase "G-tube".

Column 5, line 33 of the specification, please replace the phrase "g-tube" with the phrase "G-tube".